US00PP30789P2

(12) United States Plant Patent
Ferguson et al.

(10) Patent No.: US PP30,789 P2
(45) Date of Patent: Aug. 13, 2019

(54) STRAWBERRY PLANT VARIETY NAMED 'DRISSTRAWSIXTY'

(50) Latin Name: ***Fragaria* x *ananassa***
Varietal Denomination: DrisStrawSixty

(71) Applicant: Driscoll's, Inc., Watsonville, CA (US)

(72) Inventors: Michael D. Ferguson, Moorpark, CA (US); Josefa Lagunas, Port Hueneme, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 15/998,317

(22) Filed: Aug. 3, 2018

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/08
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson
PP22,247 P2 11/2011 Ferguson
PP23,107 P2 10/2012 Ferguson et al.

(Continued)

OTHER PUBLICATIONS

Fear et al., Unpublished U.S. Appl. No. 15/998,014, filed Jun. 11, 2018, titled "Strawberry Plant Variety Named 'DrisStrawFiftyEight'".

(Continued)

*Primary Examiner* — Keith O. Robinson
(74) *Attorney, Agent, or Firm* — Morrison & Foerster LLP

(57) ABSTRACT

A new and distinct variety of strawberry plant named 'DrisStrawSixty', particularly characterized by its yield potential, post-harvest quality of fruit, eating quality of fruit, plant size, and everbearing habit, is disclosed.

5 Drawing Sheets

(56) References Cited

U.S. PATENT DOCUMENTS

| | | | |
|---|---|---|---|
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| 2003/0079263 | P1 | 4/2003 | Gilford et al. |
| 2013/0276182 | P1 | 10/2013 | Fear et al. |

OTHER PUBLICATIONS

Ferguson et al., Unpublished U.S. Appl. No. 15/731,546, filed Jun. 26, 2017, titled "Strawberry Plant Variety Named 'DrisStrawFiftySix'".

Kibbe et al., Unpublished U.S. Appl. No. 15/731,542, filed Jun. 26, 2017, titled "Strawberry Plant Variety Named 'DrisStrawFiftyTwo'".

Kibbe et al., Unpublished U.S. Appl. No. 15/731,545, filed Jun. 26, 2017, titled "Strawberry Plant Variety Named 'DrisStrawFiftyOne'".

Mendoza, et al., Unpublished U.S. Appl.n No. 15/998,020, filed Jun. 12, 2018, titled "Strawberry Plant Variety Named 'DrisStrawSixtyOne'".

Mendoza, et al., Unpublished U.S. Appl. No. 15/998,169, filed Jul. 12, 2018, titled "Strawberry Plant Variety Named 'DrisStrawSixtyThree'".

Mendoza, et al., Unpublished U.S. Appl. No. 15/998,170, filed Jul. 12, 2018, titled "Strawberry Plant Variety Named 'DrisStrawSixtyTwo'".

Pakozdi et al., Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Stewart et al., Unpublished U.S. Appl. No. 15/731,415, filed Jun. 6, 2017, titled "Strawberry Plant Variety Named 'DrisStrawFiftyThree'".

Stewart et al., Unpublished U.S. Appl. No. 15/731,421, filed Jun. 6, 2017, titled "Strawberry Plant Variety Named 'DrisStrawFiftySeven'".

Stewart et al., Unpublished U.S. Appl. No. 15/998,031, filed Jun. 14, 2018, titled "Strawberry Plant Variety Named 'DrisStrawSixtyFour'".

Vitten et al., Unpublished U.S. Appl. No, 15/731,559, filed Jun. 27, 2017, titled "Strawberry Plant Variety Named 'DrisStrawFiftyFour'".

Vitten et al., Unpublished U.S. Appl. No. 15/731,560, filed Jun. 27, 2017, titled "Strawberry Plant Variety Named 'DrisStrawFiftyFive'".

STRAWBERRY PLANT VARIETY NAMED 'DRISSTRAWSIXTY'

Latin name:

Botanical classification: *Fragaria* x *ananassa.*

Varietal denomination: The varietal denomination of the claimed variety of strawberry plant is 'DrisStrawSixty'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSixty'.

Strawberry plant variety 'DrisStrawSixty' originated from a cross between the proprietary female parent 'DrisStraw-Seventeen' (U.S. Plant Pat. No. 22,218) and the proprietary male parent '540Q 54' (unpatented). Progeny plants from this cross, including 'DrisStrawSixty', were asexually propagated via stolons in Shasta County, Calif. in March of 2010. Strawberry plant variety 'DrisStrawSixty' was later specifically identified and selected in Ventura County, Calif. in October of 2010.

'DrisStrawSixty' was subsequently asexually propagated via stolons, and underwent testing at a farm in Ventura County, Calif. for six years. The present variety has been found to be stable and reproduce true to type through successive asexual propagations via stolons.

'DrisStrawSixty' exhibits the following distinguishing characteristics over other similar varieties when grown under normal horticultural practices in Ventura County, Calif.:

1. Semi-upright plant growth habit;
2. Medium plant vigor;
3. Shape and color of fruit; and
4. Varying resistances to pests and disease.

'DrisStrawSixty' was selected for its yield potential, post-harvest quality of fruit (e.g., fruit firmness), eating quality of fruit, plant size, and everbearing habit.

DESCRIPTION OF THE DRAWINGS

This new strawberry plant is illustrated by the accompanying photographs which show fruit of the plant, as well as the flowers and leaves. The colors shown are as true as can be reasonably obtained by conventional photographic procedures. The photographs are of plants that are 16 weeks old.

DESCRIPTION OF THE NEW VARIETY

Figure 1:
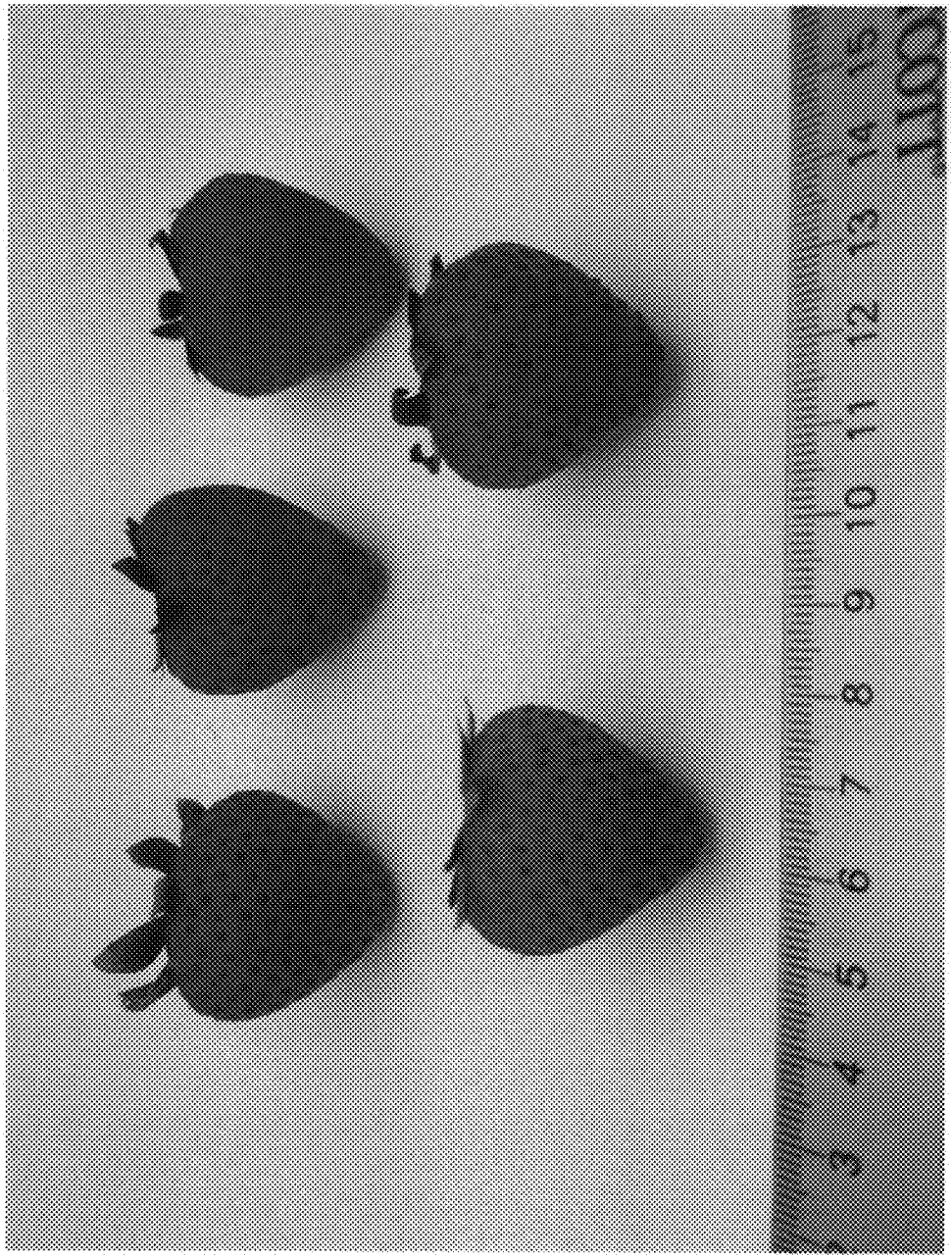
FIG. 1 illustrates whole fruit of variety 'DrisStrawSixty'.
Figure 2:
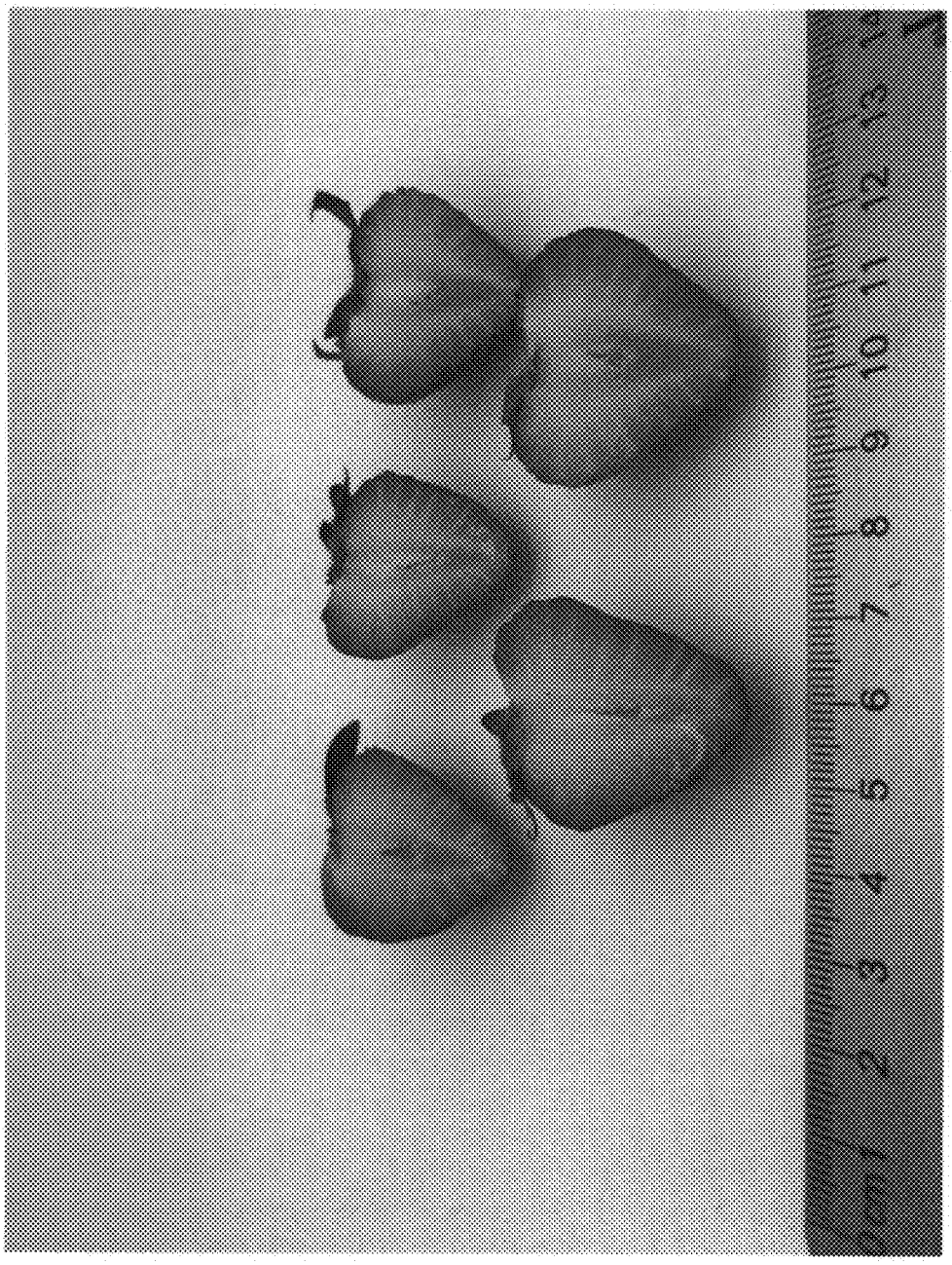
FIG. 2 illustrates longitudinal cross-sections of fruit of variety 'DrisStrawSixty'.
Figure 3:
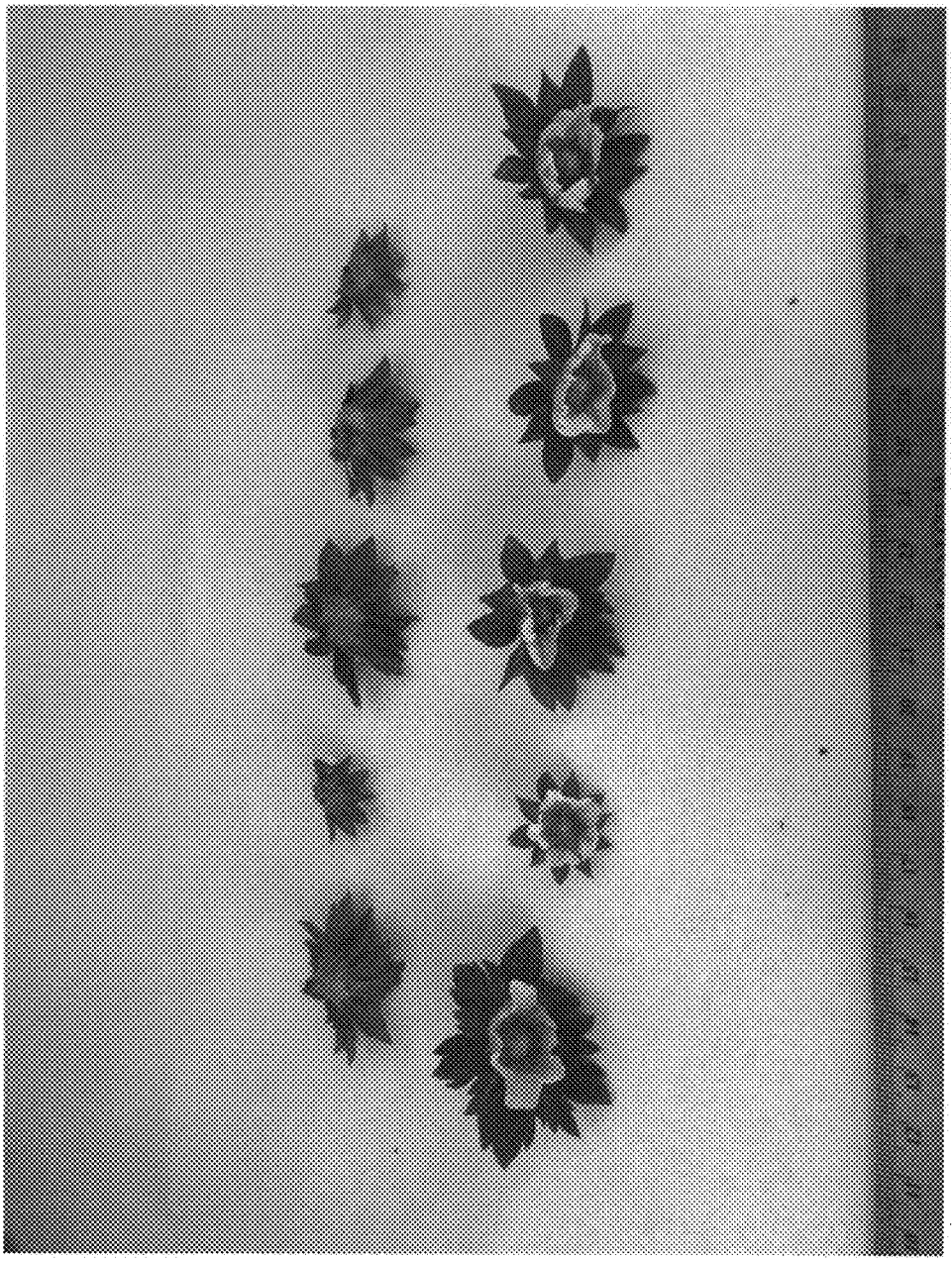
FIG. 3 illustrates the lower and upper surfaces of flowers of variety 'DrisStrawSixty'.
Figures 4A, 4B:
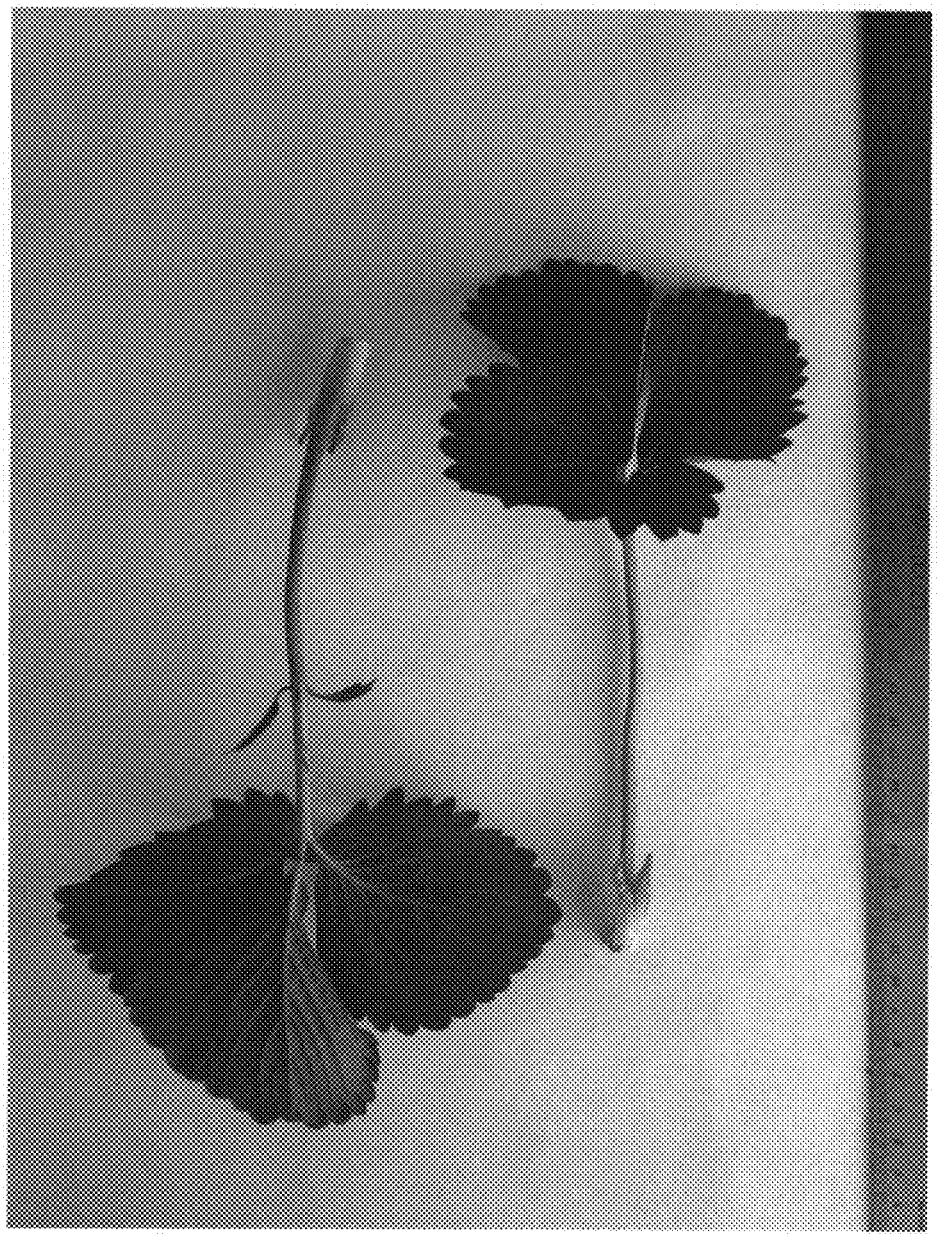
FIG. 4A illustrates the lower surface of a plant leaf of variety 'DrisStrawSixty'.
FIG. 4B illustrates the upper surface of a plant leaf of variety 'DrisStrawSixty'.
Figure 5:
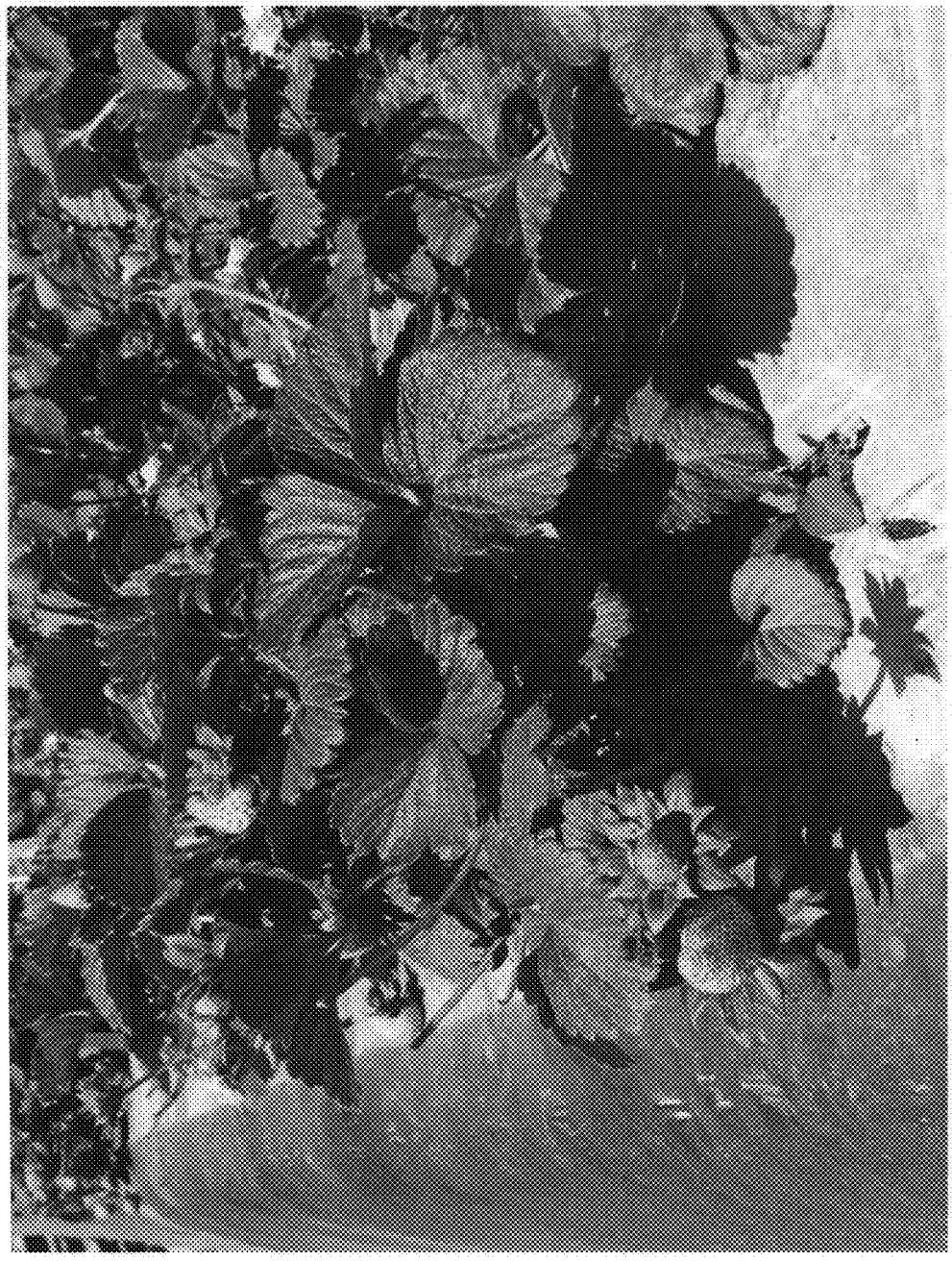
FIG. 5 illustrates the overall plant habit including fruit at various stages of development of variety 'DrisStrawSixty'.

The following detailed descriptions set forth the distinctive characteristics of 'DrisStrawSixty'. The data which define these characteristics is based on observations taken in Ventura County, Calif. for six years. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSixty' has not been observed under all possible environmental conditions. The botanical description of 'DrisStrawSixty' was taken from plants that were 16 weeks old. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria* x *ananassa.*

*Common name.*—Strawberry.

*Denomination.*—'DrisStrawSixty'.

Parentage:

*Female parent.*—The proprietary variety 'DrisStraw-Seventeen' (U.S. Plant Pat. No. 22,218).

*Male parent.*—The proprietary variety '540Q 54' (unpatented).

Plant:

*Height.*—25.2 cm.

*Diameter.*—43.9 cm.

*Number of crowns per plant.*—3.

*Growth habit.*—Semi-upright.

Stolon:

*Average number of daughter plants per square foot.*—9.

*Diameter at bract.*—0.16 mm.

*Anthocyanin coloration.*—Present.

*Anthocyanin color.*—RHS 173A (Moderate red).

Leaf:

*Number of leaflets*.—Three only.

*Color of upper surface*.—RHS 147A (Moderate olive green).

*Variegation*.—Absent.

*Terminal leaflets*.—Length: 7.1 cm. Width: 6.7 cm. Length/width ratio: 1.1. Number of teeth/terminal leaflet: 22. Shape of base: Rounded. Margin: Crenate. Shape in cross section: Convex.

*Petiole*.—Length: 11.8 cm. Diameter: 4.00 mm. Attitude of hairs: Slightly outwards to horizontal. Bract frequency (number present on each petiole): 2.

*Petiolule*.—Length: 9.81 mm. Diameter: 2.32 mm.

*Stipule*.—Length: 3.2 cm. Width: 9.29 mm. Anthocyanin coloration: Present. Anthocyanin color: RHS 58A (Moderate purplish red).

Inflorescence:

*Position in relation to foliage*.—Same level.

*Pedicel*.—Attitude of hairs: Upwards.

*Flower*.—Flower diameter (petal tip to petal tip on non-flattened flower): 23.44 mm. Arrangement of petals: Overlapping. Stamen: Present. Typical and observed number of flowers per plant: 46.00.

*Petal*.—Length: 10.06 mm. Width: 11.55 mm. Length/width ratio: 0.9. Typical and observed petal number: 6. Color of upper side: RHS 155C (Greenish white).

*Calyx*.—Diameter (sepal tip to sepal tip, measured on back of flower): 31.61 mm.

*Sepal*.—Length (sepal tip to point of attachment to receptacle): 11.04 mm. Width: 5.41 mm. Typical and observed sepal number: 11.

Fruit:

*Length*.—34.12 mm.

*Width*.—33.33 mm.

*Length/width ratio*.—1.0.

*Fruit hollow length*.—10.58 mm.

*Fruit hollow width*.—3.94 mm.

*Fruit hollow length/width ratio*.—2.7.

*Shape*.—Conical.

*Color*.—RHS 45B (Vivid red).

*Position of achenes*.—Below surface.

*Position of calyx attachment*.—Level with fruit.

*Attitude of sepals*.—Upwards.

*Color of flesh* (*excluding core*).—RHS N155D (Yellowish white).

*Color of core*.—RHS N155C (Pinkish white).

Production:

*Flowering interval*.—July to August.

*Harvest interval*.—September to December.

*Type of bearing*.—Fully remontant.

*Productivity*.—0.144 kg to 0.521 kg of fruit per plant per season from 4-month-old plants when grown in Ventura County, Calif.

Resistance to abiotic stress, pests, and diseases:

*Heat*.—Moderately resistant.

*Wind*.—Moderately resistant.

*Aphids* (*Aphis spp.*).—Moderately resistant.

*Lygus bug* (*Lygus Hesperus*).—Moderately resistant.

*Botrytis fruit rot* (*Botrytis cinerea*).—Moderately resistant.

*Powdery mildew* (*Podosphaera macularis*).—Moderately resistant.

COMPARISON WITH PARENTAL AND COMMERCIAL VARIETIES

'DrisStrawSixty' differs from the proprietary female parent 'DrisStrawSeventeen' (U.S. Plant Pat. No. 22,218) in that 'DrisStrawSixty' has medium vigor, absent or weak leaf blistering, shape in cross section of terminal leaflet that is convex, attitude of petiole hairs that is slightly outwards to horizontal, stipule anthocyanin coloration that is medium, inflorescence on the same level with foliage, and is moderately resistant to botrytis fruit rot and powdery mildew; while 'DrisStrawSeventeen' has strong vigor, medium leaf blistering, shape in cross section of terminal leaflet that is concave, attitude of petiole hairs that is upwards, stipule anthocyanin coloration that is weak, inflorescence beneath foliage, and is moderately susceptible to botrytis fruit rot and powdery mildew. Moreover, fruit of 'DrisStrawSixty' have a conical shape and achenes that are below the surface of fruit, while fruit of 'DrisStrawSeventeen' have a wedged shape and achenes that are level with surface of fruit. Additionally, fruit of 'DrisStrawSixty' have a medium red color, while fruit of 'DrisStrawSeventeen' have a dark red color.

'DrisStrawSixty' differs from the proprietary male parent '540Q 54' (unpatented) in that 'DrisStrawSixty' has lower vigor, lower yield, and smaller but firmer fruit compared to '540Q 54'.

'DrisStrawSixty' differs from the commercial variety 'DrisStrawTwentyOne'(U.S. Plant Pat. No. 23,506) in that plants of 'DrisStrawSixty' have a semi-upright growth habit, while plants of 'DrisStrawTwentyOne' have an upright growth habit. Further, plants of 'DrisStrawSixty' have medium vigor, while plants of 'DrisStrawTwentyOne' have strong vigor. Additionally, plants of 'DrisStrawSixty' have inflorescence on the same level with foliage, absent or weak blistering on leaves, and fruit that is conical in shape; while plants of 'DrisStrawTwentyOne' have inflorescence beneath foliage, medium blistering on leaves, and fruit that is biconical in shape.

'DrisStrawSixty' differs from the commercial variety 'DrisStrawThirtyOne' (U.S. Plant Pat. No. 24,317) in that plants of 'DrisStrawSixty' have a semi-upright growth habit, while plants of 'DrisStrawThirtyOne' have an upright growth habit. Further, fruit of 'DrisStrawSixty' have a medium red color and achenes below surface of fruit, while fruit of 'DrisStrawThirtyOne' have a dark red color and achenes level with surface of fruit. Additionally, 'DrisStrawSixty' is moderately resistant to aphids, lygus bug, and botrytis fruit rot, while 'DrisStrawThirtyOne' is moderately susceptible to aphids, lygus bug, and botrytis fruit rot.

We claim:

1. A new and distinct variety of strawberry plant named 'DrisStrawSixty' as shown and described herein.

* * * * *